US012702636B2

(12) United States Patent
Debeaud et al.

(10) Patent No.: US 12,702,636 B2
(45) Date of Patent: Aug. 11, 2026

(54) SOLID COMPOSITION COMPRISING SUNFLOWER WAX, CANDELILLA WAX AND NONVOLATILE ESTER OILS, AND USE THEREOF

(71) Applicant: L'OREAL, Paris (FR)

(72) Inventors: Roshanak Debeaud, Chevilly Larue (FR); Laure Jouffroy-Wendlinger, Saint-Ouen (FR)

(73) Assignee: L'OREAL, Paris (FR)

( * ) Notice: Subject to any disclaimer, the term of this patent is extended or adjusted under 35 U.S.C. 154(b) by 276 days.

(21) Appl. No.: 18/557,730

(22) PCT Filed: Apr. 27, 2022

(86) PCT No.: PCT/EP2022/061135

§ 371 (c)(1),
(2) Date: Oct. 27, 2023

(87) PCT Pub. No.: WO2022/229238

PCT Pub. Date: Nov. 3, 2022

(65) Prior Publication Data

US 2024/0366494 A1 Nov. 7, 2024

(30) Foreign Application Priority Data

Apr. 30, 2021 (FR) ...................................... 2014539

(51) Int. Cl.
*A61K 8/92* (2006.01)
*A61Q 1/06* (2006.01)

(52) U.S. Cl.
CPC ................ *A61K 8/922* (2013.01); *A61Q 1/06* (2013.01); *A61K 2800/28* (2013.01); *A61K 2800/43* (2013.01); *A61K 2800/87* (2013.01)

(58) Field of Classification Search
None
See application file for complete search history.

(56) References Cited

U.S. PATENT DOCUMENTS

2016/0175232 A1* 6/2016 El-Khouri .............. A61K 8/891
424/401
2017/0258706 A1* 9/2017 Hili ........................ A61K 8/678
2017/0349756 A1* 12/2017 Grüner ..................... A61Q 1/10
2019/0298626 A1* 10/2019 Alander ................. A61K 8/361
2020/0113791 A1* 4/2020 Manet ...................... A61Q 1/06
2020/0214950 A1* 7/2020 Fioleau .................... A61K 8/25
2020/0268627 A1* 8/2020 Yao ...................... A61K 8/0216
2021/0169771 A1* 6/2021 Schecker .............. A61K 8/345

FOREIGN PATENT DOCUMENTS

JP 2008-105951 A 5/2008
JP 2016-188191 A 11/2016
JP 2017-504613 A 2/2017
JP 2019-178074 A 10/2019
JP 2020-164446 A 10/2020
WO 2019023779 A1 2/2019
WO 2022229238 A1 11/2022

OTHER PUBLICATIONS

Radiant Lipstick 2017.*
International Search Report and Written Opinion dated Aug. 31, 2022 from International Application No. PCT/EP2022/061135 with filing date Apr. 27, 2022; 10 pages.
Mintel, "Radiant Lipstick," Feb. 2017, Database Accession No. 4597285, 11 pp, including translation.
Office Action issued Jan. 7, 2025, in Japanese Patent Application No. 2023-566661, including translation.

* cited by examiner

*Primary Examiner* — Danah Al-Awadi
(74) *Attorney, Agent, or Firm* — Womble Bond Dickinson (US) LLP

(57) ABSTRACT

The invention relates to a solid composition for making up and/or caring for the skin and/or the lips, in wand form, comprising:

sunflower wax;
candelilla wax;
at least one triglyceride chosen from triglycerides of caprylic acid, of capric acid, of caprylic/capric acid, or mixtures thereof;
at least one plant oil with the exception of castor oil; castor oil, if it is present, not exceeding a content of 5% by weight relative to the total weight of the composition;
at least one polyester derived from the condensation of a linear or branched $C_6$-$C_{10}$ dicarboxylic acid and of an ester of diglycerol and of optionally hydroxylated, linear or branched $C_6$-$C_{20}$ monocarboxylic acids.

The invention also relates to a process for making up and/or caring for the skin and/or the lips, which consists in applying said composition.

21 Claims, No Drawings

SOLID COMPOSITION COMPRISING SUNFLOWER WAX, CANDELILLA WAX AND NONVOLATILE ESTER OILS, AND USE THEREOF

The present invention relates to a solid makeup and/or care composition, in particular for the lips, which is in the form of a wand, and comprising particular plant waxes, and also ester oils, including plant oils.

Cosmetic compositions intended for care and/or makeup, in particular for the lips, have been known for a very long time and are provided in the form of more or less viscous fluids, for instance from more fluid to more viscous, oils for the lips and glosses, up to solid compositions in wand form, which may or may not be supported, compositions in pencil form, or compositions stored in jars.

Historically, compositions for the lips were generally anhydrous but, in recent years, makeup compositions for the lips which are in the form of emulsions have appeared.

By virtue of the use of film-forming products, in particular silicone products, the compositions have improved their working properties, such as enhancing the staying power or decreasing the migration.

The compositions also make it possible to obtain matt, satiny or glossy makeup results as a function in this case also of the ingredients present, for instance silicone or nonsilicone volatile oils, and mineral or organic fillers.

In recent years, a new tendency is markedly apparent among consumers, who are less exclusively, though still to a certain extent despite everything, focused on the performance qualities of the makeup composition. This is because attention is ever-increasingly focused on the ingredients used, in particular their natural character.

The present invention falls within this tendency and thus relates more particularly to solid compositions for makeup and/or care, most particularly for the lips, promoting the use of compounds of natural origin, in particular of plant origin. In addition, the compositions according to the invention advantageously make it possible to limit the content of ingredients derived in particular from petrochemistry, such as oils of hydrocarbon type, apolar hydrocarbon-based waxes, such as polyethylene or polymethylene waxes, and also of silicone ingredients.

One of the difficulties encountered with ingredients of natural origin is that natural waxes, as a result, inter alia, of their affinity with plant oils, do not always correctly structure said oils, resulting in wands that are too soft or too hard, not enabling satisfactory application of the composition and/or resulting in the wand breaking. Moreover, problems of stability of the composition, in particular on storage, may be encountered. This phenomenon can be demonstrated by the stability tests commonly employed for compositions which are in wand form. Thus, when the wand is stored in the inverted position ("head downward") at elevated temperatures (45° C.) for a period of time ranging from one week to two months, the existence of exudation of oil with the appearance of a drop of oil on the surface of the wand body, notably on the beveled end, may be observed. In point of fact, if this exudation is observed under these laboratory conditions, there is a high risk of it being repeated under the real conditions of use and of storage of lipsticks by consumers, which is clearly undesirable.

One of the objectives of the present invention is thus to propose a solid composition, more particularly in the form of a wand, which is stable, without exudation of oil(s), and which has an appropriate hardness enabling easy, regular and sufficient application of the composition, without the wand breaking. In addition, the deposit obtained has to remain comfortable and non-dehydrating and show little migration into the wrinkles and fine lines in the region around the lips.

These aims and others are achieved by the present invention, one subject of which is thus a solid composition for making up and/or caring for the skin and/or the lips, comprising:

- sunflower wax,
- candelilla wax,
- at least one triglyceride chosen from triglycerides of caprylic acid, of capric acid, of caprylic/capric acid or mixtures thereof, and preferably Caprylic/Capric Triglyceride (INCI name),
- at least one plant oil with the exception of castor oil; castor oil, if it is present, not exceeding a content of 5% by weight relative to the total weight of the composition,
- at least one polyester derived from the condensation of a linear or branched $C_6$-$C_{10}$ dicarboxylic acid and of an ester of diglycerol and of optionally hydroxylated, linear or branched $C_6$-$C_{20}$ monocarboxylic acids, preferably Bis-diglyceryl Polyacyladipate-2 (INCI name).

The invention also relates to a process for making up and/or caring for the skin and/or the lips, in particular the lips, in which the composition according to the invention is applied.

The composition according to the invention is thus stable, without any change in form or any exudation of oil, when it is stored at 4° C., 20° C. and 45° C. for 1 week, 30 days and 60 days. In addition, it retains its organoleptic properties, in particular its odor, and its color. No crystals are seen to appear at the surface of the wand body either. The composition according to the invention is moreover easy to apply, in a sufficient amount and homogeneously. It gives a precise deposit which is sparingly tacky, which migrates little and which has satisfactory staying power over time. The deposit does not dry out the lips either and it remains comfortable.

These and other advantages of the present invention will emerge more clearly on reading the description and the examples that follow.

It should be noted that, in the remainder of the description, unless otherwise indicated, the limits indicated for a range are included in that range.

The expressions "at least one" and "several" are used without distinction.

In addition, the sum of the amounts of the ingredients of the composition represents 100% of the total weight of the composition.

Protocol for Evaluating the Stability

The compositions are evaluated 24 hours after the casting of the wands, said wands having been stored at room temperature (20° C.) before the tests.

- For the stability tests, the wands are placed in an oven at 4° C., at 20° C. (room temperature) and at 45° C. for 2 months, one sample in the upright position (upper part of the wand "at the top"—"head upward"), another sample in the inverted position (upper part of the wand "at the bottom"—"head downward").
- The appearance, color and odor are analyzed for each sample, before the start of the test, after a week, after a month and finally after two months of stability. After having been observed, each sample is placed back as is (in particular without having been wiped), in its oven and in its initial position, until the following analysis.

At each analytical step, the wands undergo a first Appearance/Color/Odor observation immediately after being taken out of the oven, and then a second observation, for those stored at 4° C. and at 45° C., once they have reached room temperature.

Exudation corresponds to the appearance, on the wand, of drop(s) of oil, gelled or not, on the surface of the wand (wand body). It is enhanced when the wand is stored in the head downward position; the drop then appears at the end of the wand body. This phenomenon is to be distinguished from another transient phenomenon (known as sweating) which may possibly appear during rapid changes in temperature (for example when the wand body stored at 4° C. returns to room temperature), notably on wands at least 1 month old. This sweating is exhibited by the appearance of numerous fine droplets distributed over the whole of the wand body.

Protocol for Measuring the Hardness

The hardness of the composition is measured according to the following protocol:

The lipstick is stored at 20° C. for 16 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the wand at a speed of 100 mm/minute.

The hardness of the samples of compositions of the invention, expressed in $Nm^{-1}$, is measured using a DFGS2 tensile testing machine sold by the company Indelco-Chatillon.

The measurement is repeated three times and then averaged. The average of the three values read using the tensile testing machine mentioned above, noted Y, is given in grams.

This average is converted into newtons and then divided by L which represents the longest distance through which the wire passes. In the case of a cylindrical wand, L is equal to the diameter (in meters).

The hardness is converted into $Nm^{-1}$ by the equation below:

$$(Y\times 10^{-3}\times 9.8)/L$$

For a measurement at a different temperature, the wand is stored for 24 hours at this new temperature before the measurement.

According to this measuring method, the composition according to the invention preferably has a hardness at 20° C. and at atmospheric pressure of between 70 and 200 $Nm^{-1}$, advantageously between 75 and 195 $Nm^{-1}$ and preferably between 100 and 160 $Nm^{-1}$.

Sunflower Wax

As indicated previously, the composition according to the invention comprises at least sunflower wax.

Sunflower wax (INCI name: *Helianthus annuus* (sunflower) Seed Wax) is obtained from sunflower seeds. It is notably sold by the company Koster Keunen.

More particularly, the composition according to the invention has a sunflower wax content of between 1% and 9% by weight, relative to the total weight of the composition, preferably between 2% and 8% by weight relative to the total weight of the composition.

Candelilla Wax

The present invention also comprises candelilla wax (INCI name: *Euphorbia cerifera* (candelilla) Wax). It is notably sold by the company Multiceras.

More particularly, the composition according to the invention has a candelilla wax content of between 0.25% and 7% by weight, relative to the total weight of the composition, preferably between 0.5% and 6% by weight, more particularly from 1.5% to 6% by weight relative to the total weight of the composition.

Additional Waxes

Polar Waxes

The composition according to the invention may optionally comprise at least one additional polar hydrocarbon-based wax, other than sunflower wax and candelilla wax.

More particularly, it is recalled that a wax is in general a lipophilic compound that is solid at room temperature (20° C.), with a reversible solid/liquid change of state, having a melting point in particular greater than or equal to 40° C. and less than or equal to 120° C., more particularly less than or equal to 90° C.

For the purposes of the invention, the melting point corresponds to the temperature of the most endothermic peak observed on thermal analysis (DSC) as described in the standard ISO 11357-3; 1999.

The melting point of the wax may be measured using a differential scanning calorimeter (DSC), for example the calorimeter sold under the name DSC Q2000 by the company TA Instruments with the TA Universal Analysis software.

The Measuring Protocol is as Follows:

A sample of 5 mg of wax placed in a crucible is subjected to a first temperature rise ranging from −20° C. to 120° C., at a heating rate of 10° C./minute, it is then cooled from 120° C. to −20° C. at a cooling rate of 10° C./minute and is finally subjected to a second temperature rise ranging from −20° C. to 120° C. at a heating rate of 5° C./minute.

During the second temperature rise, the melting point of the solid fatty substance is measured, which corresponds to the temperature of the most endothermic peak observed of the melting curve, representing the variation in the difference in power absorbed as a function of the temperature.

The enthalpy of fusion of the wax (ΔHf), corresponding to the integral of the entire melting curve obtained, may also be measured. This heat of fusion of the wax is the amount of energy required to make the compound change from the solid state to the liquid state. It is expressed in J/g.

More particularly, the additional polar hydrocarbon-based wax is chosen from hydrocarbon-based waxes, comprising an ester function.

The term "polar hydrocarbon-based wax" means a wax formed essentially from, or even constituted of, carbon and hydrogen atoms, and comprising at least one oxygen, optionally nitrogen, atom. These compounds thus do not contain any silicon atoms.

According to the invention, the term "ester wax" means a wax comprising at least one ester function. The ester waxes may also be hydroxylated.

Among the polar hydrocarbon-based waxes that may be used in the context of the present invention, mention may be made of:

(i) waxes of formula $R_1COOR_2$ in which $R_1$ and $R_2$ represent linear, branched or cyclic aliphatic chains, the number of atoms of which ranges from 10 to 50, which may contain a heteroatom, in particular oxygen, and the melting point of which ranges from 40° C. to 120° C., preferably from 40° C. to 100° C. In particular, use may be made, as an ester wax, of a $C_{20}$-$C_{40}$ alkyl (hydroxystearyloxy)stearate (the alkyl group comprising from 20 to 40 carbon atoms), alone or as a mixture, or a $C_{20}$-$C_{40}$ alkyl stearate. Such waxes are notably sold under the names Kester Wax® K 82 P, Hydroxypolyester® K 82 P, Kester Wax® K 80 P and Kester Wax® K82H by the company Koster Keunen. Use may also be made of mixtures of esters of $C_{14}$-$C_{18}$ carboxylic acids and of alcohols, such as the products Cetyl Ester Wax 814 from the company Koster Keunen, SP Crodamol MS MBAL and Crodamol MS PA from the company Croda, and Miraceti from the company Laserson.

(ii) Diester waxes of a dicarboxylic acid of general formula $R_3$—(—OCO—$R_4$—COO—$R_5$), in which $R_3$ and $R_5$ are identical or different, preferably identical, and represent a $C_4$-$C_{30}$ alkyl group and $R_4$ represents a linear or branched $C_4$-$C_{30}$ aliphatic group which may or may not contain one or more unsaturations. Preferably, the $C_4$-$C_{30}$ aliphatic group is linear and unsaturated.

(iii) Partial or total, preferably total, esters of a saturated, optionally hydroxylated, $C_{16}$-$C_{30}$ carboxylic acid with glycerol, for instance glyceryl tristearate (INCI name: Tristearin), glyceryl trihydroxystearate (INCI name: Trihydroxystearin), glyceryl tribehenate (INCI name: Tribehenin), alone or as a mixture.

(iv) Waxes of animal or plant origin. As examples of waxes that are suitable for use, mention may be made of beeswax, carnauba wax, macadamia wax, lanolin wax, rice bran wax, ouricury wax, esparto grass wax, shellac wax, cork fiber wax, sugar cane wax, Japan wax (ICNI name: *Rhus verniciflua* Peel Wax), sumac wax, montan wax, orange wax and lemon wax, which may or may not be refined.

(v) Waxes obtained by hydrogenation of animal or plant oils. Mention may be made more particularly of the waxes obtained by catalytic hydrogenation of plant oils notably containing linear or branched $C_8$-$C_{32}$ fatty chains, for instance hydrogenated jojoba oil, hydrogenated sunflower oil, hydrogenated castor oil or hydrogenated camelina oil, and also the waxes obtained by hydrogenation of castor oil esterified with cetyl alcohol or behenyl alcohol, such as those sold under the names Phytowax® Ricin 16L64 and Phytowax® Ricin 22L73 by the company Sophim. Such waxes are described in patent application FR 2 792 190. As waxes obtained by hydrogenation of olive oil esterified with stearyl alcohol or lauryl alcohol, mention may be made of those sold under the name Phytowax® Olive 18 L 57 or Phytowax® Olive 12 L 44.

(vi) mixtures thereof.

Preferably, if the composition comprises any, the additional polar hydrocarbon-based wax(es) are chosen from waxes of animal or plant origin, other than sunflower wax and candelilla wax; waxes obtained by hydrogenation of animal or plant oils, and also mixtures thereof. More particularly, the additional hydrocarbon-based polar wax(es) are chosen from beeswax, carnauba wax, rice bran wax, ouricury wax, esparto grass wax, Japan wax, shellac wax, cork fiber wax, sugarcane wax, sumac wax, montan wax, orange wax and lemon wax; from hydrogenated jojoba oil, hydrogenated sunflower oil, hydrogenated castor oil, hydrogenated camellina oil, and also waxes obtained by hydrogenation of esterified castor oil; and also mixtures thereof.

If the composition according to the invention comprises one or more additional polar hydrocarbon-based waxes, other than sunflower wax and candelilla wax, their content represents from 0.25% to 9% by weight, more particularly 0.5% to 8% by weight, preferably from 1.5% to 8% by weight, relative to the total weight of the composition.

Additional Apolar Waxes

Preferably, the composition according to the invention does not comprise any apolar hydrocarbon-based waxes (in other words waxes constituted solely of carbon and hydrogen atoms). Examples that may be mentioned include the waxes resulting from the conversion of petroleum, for instance polyethylene waxes, polymethylene waxes (INCI name: Synthetic Wax, Fischer-Tropsch waxes) or paraffin waxes; also waxes of ceresin or ozokerite type; alone or as mixtures.

If, however, the composition were to comprise any, their content would not exceed 2% by weight, preferably would not exceed 1% by weight and advantageously would not exceed 0.5% by weight, relative to the total weight of the composition.

Finally, according to a particularly advantageous embodiment of the present invention, the total content of polar waxes ranges between 6% and 26% by weight and preferably between 6% and 18% by weight relative to the total weight of the composition.

Solid Polyester

The composition according to the invention comprises at least one polyester that is solid at room temperature, more particularly pasty, resulting from the condensation of a linear or branched $C_6$-$C_{10}$ dicarboxylic acid and an ester of diglycerol and of linear or branched, optionally hydroxylated $C_6$-$C_{20}$ monocarboxylic acids. As a particular example, the diester obtained by condensation of adipic acid and of a mixture of esters of diglycerol with a mixture of $C_6$-$C_{20}$ fatty acids such as caprylic acid, capric acid, stearic acid, isostearic acid and 12-hydroxystearic acid, and having the INCI name Bis-diglyceryl Polyacyladipate-2, is suitable for performing the invention. This type of compound is notably sold under the reference Softisan® 649 by the company Cremer Oleo.

According to a particular embodiment of the invention, the content of solid polyester is advantageously between 5% and 35% by weight and preferably between 7% and 25% by weight relative to the total weight of the composition.

Pasty Hydrocarbon-Based Compounds

The composition according to the invention may optionally comprise at least one pasty hydrocarbon-based compound other than the abovementioned solid polyester.

The term "hydrocarbon-based" refers to a compound formed essentially from, or even constituted of, carbon and hydrogen atoms, and also comprising at least one oxygen, optionally nitrogen, atom. Compounds of this type are thus different from silicone compounds.

For the purposes of the present invention, the term "pasty compound" means a lipophilic fatty compound with a reversible solid/liquid change of state, and including at a temperature of 20° C. a liquid fraction and a solid fraction. Thus, a pasty compound may have a starting melting point of less than 20° C. Moreover, the pasty compound may have, in the solid state, an anisotropic crystalline organization. The melting point of the pasty fatty substance is determined according to the same principle as that detailed previously for the waxes. In the case of a pasty compound, the measuring protocol is, however, as follows:

A sample of 5 mg of pasty fatty substance placed in a crucible is subjected to a first temperature rise ranging from −20° C. to 100° C., at a heating rate of 10° C./minute, it is then cooled from 100° C. to −20° C. at a cooling rate of 10° C./minute and it is finally subjected to a second temperature rise ranging from −20° C. to 100° C. at a heating rate of 5° C./minute.

The melting point of the pasty fatty substance is the value of the temperature corresponding to the top of the peak on the curve representing the variation in the difference in power absorbed as a function of the temperature.

It should be noted that the liquid fraction by weight of the pasty fatty substance at room temperature is equal to the ratio of the heat of fusion consumed at room temperature to the heat of fusion of the pasty fatty substance.

The heat of fusion of the pasty fatty substance is the heat consumed by said substance in order to pass from the solid state to the liquid state. The pasty fatty substance is said to be in the solid state when all of its mass is in crystalline solid form. The pasty fatty substance is said to be in the liquid state when all of its mass is in liquid form.

The heat of fusion of the pasty fatty substance is the amount of energy required to make the pasty fatty substance change from the solid state to the liquid state. It is expressed in J/g. The heat of fusion of the pasty fatty substance is equal to the area under the curve of the thermogram obtained.

Preferably, this or these pasty hydrocarbon-based compound(s) are chosen from:

- plant butters, for instance mango butter, such as the product sold under the reference Lipex® 203 by the company Aarhuskarlshamn, shea butter, in particular the product whose INCI name is *Butyrospermum parkii* Butter, such as the product sold under the reference Sheasoft® by the company Aarhuskarlshamn, cupuacu butter (Rain Forest RF3410 from the company Beraca Sabara), murumuru butter (Rain Forest RF3710 from the company Beraca Sabara), cocoa butter; babassu butter such as the product sold under the name Cropure® Babassu by Croda, and also orange wax, for example the product sold under the reference Orange Peel Wax by the company Koster Keunen,
- totally or partially hydrogenated plant oils, for instance hydrogenated soybean oil, hydrogenated coconut kernel oil, hydrogenated rapeseed oil, mixtures of hydrogenated plant oils such as the mixture of hydrogenated soybean, coconut kernel, palm and rapeseed plant oil, for example the mixture sold under the reference Akogel® by the company Aarhuskarlshamn (INCI name Hydrogenated Vegetable Oil), the trans-isomerized partially hydrogenated jojoba oil manufactured or sold by the company Desert Whale under the commercial reference Iso-Jojoba-50®, partially hydrogenated olive oil, for instance the compound sold under the reference Beurrolive by the company Soliance,
- esters of hydrogenated castor oil and of $C_{16}$-$C_{22}$ fatty acids, in particular of isostearic acid, for instance Hydrogenated Castor Oil Isostearate (INCI name) Salacos HCIS (V-L), sold by the company Nisshin Oil,
- triglycerides of fatty acids which are optionally hydrogenated (totally or partially), saturated or unsaturated, linear or branched, optionally mono- or polyhydroxylated, preferably $C_{12}$-$C_{18}$, for instance the glycerides of saturated $C_{12}$-$C_{18}$ fatty acids sold under the name Softisan 100® by the company Cremer Oleo (INCI name: Hydrogenated Coco-Glycerides),
- esters of diol dimer, of alcohol or of polyol, and of dimer of acid, for instance:
- esters of dimer diol (eg.: dilinoleyl alcohol) and of dilinoleic acid, the hydroxyl groups of which are esterified with a mixture of phytosterols, of behenyl alcohol and of isostearyl alcohol, for example the esters with INCI name Bis-Behenyl/Isostearyl/Phytosteryl Dimer Dilinoleyl Dimer Dilinoleate, particularly sold under the name Plandool G by the company Nippon Fine Chemical;
- esters of dilinoleic acid and of a mixture of phytosterols, of isostearyl alcohol, of cetyl alcohol, of stearyl alcohol and of behenyl alcohol, for example the esters with INCI name: Phytosteryl/Isostearyl/Cetyl/Stearyl/Behenyl Dimer Dilinoleate particularly sold under the name Plandool H or Plandool S by the company Nippon Fine Chemical;
- esters of hydrogenated castor oil and of dilinoleic acid, such as Hydrogenated Castor Oil Dimer Dilinoleate (INCI name) such as those sold under the names Risocast-DA-L or Risocast-DA-H by the company Kokyu Alcohol Kogyo.

Preferably, if the composition comprises any, the pasty hydrocarbon-based compound(s) are chosen from plant butters, partially hydrogenated plant oils, triglycerides of linear or branched, saturated or unsaturated, optionally monohydroxylated or polyhydroxylated, preferably $C_{12}$-$C_{18}$ fatty acids, and mixtures thereof.

Even more preferably, if the composition comprises any, the pasty hydrocarbon-based compound(s) are chosen from plant butters, partially or totally hydrogenated plant oils, the compounds with the INCI name Hydrogenated Coco-Glycerides, and also mixtures thereof.

If the composition comprises at least one pasty hydrocarbon-based compound, other than the solid polyester, their content is such that the amount of solid polyester and of pasty hydrocarbon-based compound(s) ranges from 5% to 35% by weight, preferably from 7% to 25% by weight, relative to the total weight of the composition.

Moreover, if the composition comprises, as pasty hydrocarbon-based compound(s), at least one compound chosen from esters of diol dimer, or of alcohol or of polyol and of diacid dimer, in particular at least one of the compounds with the following INCI names: Bis-Behenyl/Isostearyl/Phytosteryl Dimer Dilinoleyl Dimer Dilinoleate, Phytosteryl/Isostearyl/Cetyl/Stearyl/Behenyl Dimer Dilinoleate, Hydrogenated Castor Oil Dimer Dilinoleate, and also mixtures thereof, then their content would be between 1% and 15% by weight, more particularly between 2% and 12% by weight, relative to the total weight of the composition; the content of solid polyester and of pasty hydrocarbon-based compound(s) remaining between 5% and 35% by weight, preferably from 7% to 25% by weight, relative to the total weight of the composition.

Triglycerides

As indicated previously, the composition comprises at least one triglyceride chosen from caprylic acid triglyceride, capric acid triglyceride, caprylic/capric acid triglyceride (more particularly a triglyceride of a mixture of caprylic and capric acids) or mixtures thereof. These triglycerides are liquid at room temperature (20° C.) and atmospheric pressure ($1.013\times10^5$ Pa). Preferably, the composition comprises at least one caprylic/capric acid triglyceride (INCI name: Caprylic/capric Triglyceride). This product is notably sold by the companies Musim Mas, KLK Oleo and Stearinerie Dubois.

Preferably, the content of triglyceride(s) is at least 10% by weight, relative to the total weight of the composition. Advantageously, the content of triglyceride(s) ranges from 10% to 35% by weight relative to the total weight of the composition, preferably from 15% to 25% by weight relative to the total weight of the composition.

Plant Oils

The composition according to the invention also comprises at least one plant oil, with the exception of castor oil.

It should firstly be recalled that the term "plant oil" means a compound which is in a liquid form at room temperature (20° C.) and atmospheric pressure ($1.013\times10^5$ Pa).

As regards castor oil, if the composition comprises any, then its content does not exceed 5% by weight, preferably does not exceed 2% by weight, more particularly does not exceed 1% by weight, relative to the total weight of the composition. In accordance with an even more advantageous embodiment, the content of castor oil, if such an oil were present in the composition, would not exceed 0.5% by weight, notably would not exceed 0.1% by weight, relative to the total weight of the composition. Preferably, the composition is free of castor oil.

Among the plant oil(s) that are suitable for use in the present invention, with the exception of castor oil, mention may be made of of olive oil, coco oil, coconut oil, coconut kernel oil, jojoba oil, ximenia oil, annatto oil, pracaxi oil, coriander seed oil, macadamia oil, passionflower oil, argan oil, sesame oil, sunflower oil, grape seed oil, avocado oil, Rosa canina oil, apricot kernel oil, linseed oil, sweet almond oil, cottonseed oil, soybean oil, rapeseed oil, groundnut oil, kaya oil, marula oil, camelina oil, wheat germ oil, maize oil, maize germ oil, rice bran oil, alfalfa oil, poppy oil, pumpkin oil, marrow oil, hazelnut oil, blackcurrant oil, evening primrose oil, millet oil, barley oil, quinoa oil, rye oil, safflower oil, candlenut oil, limnanthes oil, black cumin oil, buriti oil, sandalwood nut oil, babassu oil, the liquid fraction of shea butter, and the liquid fraction of cocoa butter, and also mixtures thereof.

Preferably, the plant oil(s) are chosen from olive oil, coconut oil, jojoba oil, ximenia oil, macadamia oil, sesame oil, sunflower oil, grape seed oil, avocado oil, apricot kernel oil, linseed oil, sweet almond oil, cottonseed oil, soybean oil, rapeseed oil, groundnut oil, wheat germ oil, maize germ oil, rice bran oil, alfalfa oil, safflower oil, limnanthes oil, the liquid fraction of shea butter, and the liquid fraction of cocoa butter, and also mixtures thereof.

More particularly, the content of plant oil(s), with the exception of castor oil, is at least 3% by weight, more particularly at least 5% by weight; advantageously, it ranges from 5% to 65% by weight, relative to the total weight of the composition, preferably from 10% to 55% by weight, relative to the total weight of the composition.

Additional Liquid Compounds

The composition according to the invention may optionally comprise at least one additional, volatile or nonvolatile, hydrocarbon-based or silicone oil other than the capric and/or caprylic triglyceride(s), the plant oils and the castor oil described previously.

The term "nonvolatile oil" denotes compounds that are liquid at 20° C. and atmospheric pressure ($1.013\times10^5$ Pa), whose vapor pressure at 20° C. is nonzero and is less than 2.66 Pa and more particularly less than 0.13 Pa. By way of example, the vapor pressure may be measured according to the static method or via the effusion method by isothermal thermogravimetry, depending on the vapor pressure (standard OCDE 104).

The term "volatile oil" denotes an oil with a nonzero vapor pressure, at room temperature and atmospheric pressure, ranging in particular from 2.66 Pa to 40 000 Pa, in particular ranging up to 13 000 Pa and more particularly ranging up to 1300 Pa.

The term "hydrocarbon-based oil" means an oil formed essentially from, or even constituted of, carbon and hydrogen atoms, and also comprising at least one oxygen, optionally nitrogen, atom. These oils are thus different from silicone oils.

The term "silicone oil" denotes an oil containing at least one silicon atom, and notably containing Si—O groups.

Preferably, the composition according to the invention comprises limited contents of volatile or nonvolatile silicone oils, and also of volatile or nonvolatile apolar hydrocarbon-based oils (in other words oils comprising only carbon and hydrogen atoms) resulting from the conversion of petroleum.

As volatile or nonvolatile silicone oils, examples that may be mentioned include volatile linear or cyclic silicones, polydimethylsiloxanes (INCI name: Dimethicone) and phenyl silicones.

As examples of apolar hydrocarbon-based oils, mention may notably be made of volatile linear or branched apolar hydrocarbon-based oils containing from 8 to 16 carbon atoms and mixtures thereof, hydrogenated or nonhydrogenated poly(iso)butenes, hydrogenated or nonhydrogenated polydecenes, liquid paraffins and also mixtures thereof.

More particularly, if the composition comprises any, the content of silicone oil(s) and of apolar hydrocarbon-based oil(s) resulting from the conversion of petroleum is less than or equal to 7% by weight, more particularly less than 5% by weight, relative to the total weight of the composition. In accordance with an advantageous embodiment of the invention, the content of silicone oil(s) and of apolar hydrocarbon-based oil(s) resulting from the conversion of petroleum is less than or equal to 2% by weight, more particularly less than 1% by weight, relative to the total weight of the composition, and preferably the composition is free of said oils.

The composition according to the invention may optionally comprise as additional hydrocarbon-based oils, which are in particular nonvolatile, squalane of plant origin, the compound C15-19 Alkane (INCI name), and also nonvolatile polar hydrocarbon-based oils chosen from $C_{10}$-$C_{26}$ alcohols, nonvolatile hydrocarbon-based oils of ester type comprising at least 10 carbon atoms, dicaprylyl ether, dicaprylyl carbonate, and also mixtures thereof.

Among the saturated or unsaturated, linear or branched, $C_{10}$-$C_{26}$ fatty alcohols, preferably monoalcohols, mention may be made of lauryl alcohol, isostearyl alcohol, oleyl alcohol, 2-butyloctanol, 2-undecylpentadecanol, 2-hexyldecyl alcohol, isocetyl alcohol, octyldodecanol and mixtures thereof.

As regards nonvolatile hydrocarbon-based oils of ester type, mention may be made of:

- linear aliphatic hydrocarbon-based esters of formula RCOOR' in which RCOO represents a carboxylic acid residue including from 2 to 40 carbon atoms and R' represents a hydrocarbon-based chain containing from 1 to 40 carbon atoms, aliphatic hydrocarbon-based esters of alkylene glycol, in particular ethylene glycol or propylene glycol, the total number of carbon atoms advantageously being at least 10. As examples of such esters, mention may notably be made of cetostearyl octanoate, isopropyl myristate, isopropyl palmitate, isopropyl stearate or isostearate, ethyl palmitate, 2-ethylhexyl palmitate, isostearyl isostearate, octyl stearate, isostearyl heptanoate, octanoates, decanoates or ricinoleates of alcohols or of polyalcohols, such as propylene glycol dioctanoate, cetyl octanoate or tridecyl octanoate, 2-ethylhexyl palmitate, alkyl benzoate, polyethylene glycol diheptanoate, propylene glycol bis (2-ethylhexanoate) and mixtures thereof, hexyl laurate, neopentanoic acid esters, such as isodecyl neopentanoate, isotridecyl neopentanoate, isostearyl neopentanoate or 2-octyldodecyl neopentanoate, isononanoic acid esters, such as isononyl isononanoate, isotridecyl isononanoate or octyl isononanoate, oleyl erucate, isopropyl lauroyl sarcosinate, diisopropyl sebacate, isocetyl stearate, isodecyl neopentanoate, isostearyl behenate or myristyl myristate;
- hydroxylated esters such as polyglyceryl-2 triisostearate;
- aromatic esters such as tridecyl trimellitate, $C_{12}$-$C_{15}$ alcohol benzoate, the 2-phenylethyl ester of benzoic acid, and butyloctyl salicylate;
- linear fatty acid esters with a total carbon number ranging from 35 to 70, for instance pentaerythrityl tetrapelargonate;
- esters of $C_{24}$-$C_{28}$ branched fatty acids or fatty alcohols such as triisoarachidyl citrate, pentaerythrityl tetraisononanoate, glyceryl triisostearate, glyceryl tris(2-decyltetradecanoate), pentaerythrityl tetraisostearate, polyglyceryl-2 tetraisostearate or pentaerythrityl tetrakis(2-decyltetradecanoate);
- the polyesters obtained by condensation of dimer and/or trimer of unsaturated fatty acid and of diol, such as those with the INCI name Dilinoleic Acid/Butanediol Copolymer or Dilinoleic Acid/Propanediol Copolymer; the polyesters obtained by condensation of fatty acid dimer and of diol dimer, such as the product with the INCI name Dimer Dilinoleyl Dimer Dilinoleate;
- mixtures thereof.

Preferably, the additional hydrocarbon-based oil(s), which are in particular nonvolatile, are chosen from squalane of plant origin, the compound C15-19 Alkane (INCI name), nonvolatile hydrocarbon-based oils of ester type comprising at least 10 carbon atoms, and also mixtures thereof.

If the composition comprises such additional nonvolatile polar hydrocarbon-based oils, their content ranges from 1% to 20% by weight, relative to the total weight of the composition.

It should be noted that, if the composition comprises at least one additional nonvolatile polar hydrocarbon-based oil chosen from $C_{10}$-$C_{26}$ alcohols, their content is advantageously between 1% and 7% by weight, relative to the total weight of the composition.

Dyestuffs

According to a particular embodiment of the invention, the composition comprises at least one dyestuff, which is synthetic, natural or of natural origin.

The dyestuff may be chosen from coated or uncoated pigments, liposoluble dyes, and mixtures thereof.

Pigments

The term “pigments” means white or colored, mineral or organic particles, which are insoluble in an aqueous medium, and which are intended to color and/or opacify the resulting composition and/or deposit.

According to a particular embodiment, the pigments used according to the invention are chosen from mineral pigments.

The term “mineral pigment” means any pigment that satisfies the definition in Ullmann’s encyclopedia in the chapter on inorganic pigments. Among the mineral pigments that are useful in the present invention, mention may be made of zirconium oxide or cerium oxide, and also zinc oxide, iron oxide (black, yellow or red) or chromium oxide, manganese violet, ultramarine blue, chromium hydrate and ferric blue, titanium dioxide, and metal powders, for instance aluminum powder and copper powder. The following mineral pigments may also be used: $Ta_2O_5$, $Ti_3O_5$, $Ti_2O_3$, TiO, $ZrO_2$ as a mixture with $TiO_2$, $ZrO_2$, $Nb_2O_5$, $CeO_2$, ZnS.

The size of the pigment that is useful in the context of the present invention is generally greater than 100 nm and may range up to 10 μm, preferably from 200 nm to 5 μm and more preferentially from 300 nm to 1 μm. According to a particular form of the invention, the pigments have a size characterized by a D [50] of greater than 100 nm and possibly ranging up to 10 μm, preferably from 200 nm to 5 μm and more preferentially from 300 nm to 1 μm. The sizes are measured by static light scattering using a commercial MasterSizer 3000® particle size analyzer from Malvern, which makes it possible to determine the particle size distribution of all of the particles over a wide range which may extend from 0.01 μm to 1000 μm. The data are processed on the basis of the standard Mie scattering theory. This theory is the most suitable for size distributions ranging from submicron to multimicron; it allows an “effective” particle diameter to be determined. This theory is notably described in the publication by Van de Hulst, H. C., *Light Scattering by Small Particles,* Chapters 9 and 10, Wiley, New York, 1957. D [50] represents the maximum size exhibited by 50% by volume of the particles.

In the context of the present invention, the mineral pigments are more particularly iron oxide and/or titanium dioxide. Examples that may be mentioned more particularly include titanium dioxide and iron oxide coated with aluminum stearoyl glutamate, sold, for example, under the reference NAI® by the company Miyoshi Kasei.

As mineral pigments that may be used in the invention, mention may also be made of nacres.

The term “nacres” should be understood as meaning colored particles of any form, which may or may not be iridescent, notably produced by certain molluscs in their shell, or alternatively synthesized, and which have a color effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic dyestuffs.

Examples of nacres that may also be mentioned include natural mica covered with titanium oxide, with iron oxide, with natural pigment or with bismuth oxychloride.

The nacres may more particularly have a yellow, pink, red, bronze, orange, brown, gold and/or coppery color or tint.

Among the pigments that may be used according to the invention, mention may also be made of those having an optical effect different from a simple conventional coloring effect, i.e. a unified and stabilized effect such as produced by conventional dyestuffs, for instance monochromatic pigments.

For the purposes of the invention, the term “stabilized” means lacking the effect of variability of the color with the angle of observation or in response to a temperature change.

For example, this material may be chosen from particles with a metallic tint, goniochromatic coloring agents, diffractive pigments, thermochromic agents, optical brighteners, and also fibers, notably interference fibers. Needless to say, these various materials may be combined in order simultaneously to afford two effects, or even a novel effect in accordance with the invention.

According to a particular embodiment, the composition according to the invention comprises at least one uncoated pigment.

According to another particular embodiment, the composition according to the invention comprises at least one pigment coated with at least one lipophilic or hydrophobic compound. This type of pigment is particularly advantageous. Insofar as they are treated with a hydrophobic compound, they show predominant affinity for an oily phase, which can then convey them. The coating may also comprise at least one additional non-lipophilic compound. For the purposes of the invention, the “coating” of a pigment according to the invention generally denotes the total or partial surface treatment of the pigment with a surface agent, absorbed, adsorbed or grafted onto said pigment.

The surface-treated pigments may be prepared according to surface treatment techniques of chemical, electronic, mechanochemical or mechanical nature that are well known to a person skilled in the art. Commercial products may also be used.

The surface agent may be absorbed, adsorbed or grafted onto the pigments by evaporation of solvent, chemical reaction and creation of a covalent bond. According to one variant, the surface treatment consists of coating the pigments.

The coating may represent from 0.1% to 20% by weight and in particular from 0.5% to 5% by weight relative to the total weight of the coated pigment. The coating may be produced, for example, by adsorption of a liquid surface agent onto the surface of the solid particles by simple mixing with stirring of the particles and of said surface agent, optionally with heating, prior to the incorporation of the particles into the other ingredients of the makeup or care composition.

The coating may be produced, for example, by chemical reaction of a surface agent with the surface of the solid pigment particles and creation of a covalent bond between the surface agent and the particles. This method is notably described in patent U.S. Pat. No. 4,578,266.

The chemical surface treatment may consist in diluting the surface agent in a volatile solvent, dispersing the pigments in this mixture and then slowly evaporating off the volatile solvent, so that the surface agent is deposited on the surface of the pigments.

According to a particular embodiment of the invention, the pigments may be coated according to the invention with at least one compound chosen from silicone surface agents; fluoro surface agents; fluorosilicone surface agents; metal soaps; N-acylamino acids or salts thereof; lecithin and derivatives thereof; isopropyl triisostearyl titanate; isostearyl sebacate; natural plant or animal waxes; polar synthetic waxes; fatty esters; phospholipids; and mixtures thereof.

According to a particular embodiment of the invention, the pigments may be coated with a hydrophilic compound.

According to a particular embodiment, the dyestuff is an organic pigment, which is synthetic, natural or of natural origin.

The term “organic pigment” refers to any pigment that satisfies the definition in Ullmann’s encyclopedia in the chapter on organic pigments. The organic pigment may notably be chosen from nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane and quinophthalone compounds.

The organic pigment(s) may be chosen, for example, from carmine, carbon black, aniline black, melanin, azo yellow, quinacridone, phthalocyanine blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenol derivatives as described in patent FR 2 679 771.

The pigments may also be in the form of composite pigments as described in patent EP 1 184 426. These composite pigments may notably be composed of particles including a mineral core at least partially covered with an organic pigment and at least one binder for fixing the organic pigments to the core.

The pigment may also be a lake.

The term “lake” means insolubilized dyes adsorbed onto insoluble particles, the assembly thus obtained remaining insoluble during use.

The mineral substrates onto which the dyes are adsorbed are, for example, alumina, silica, calcium sodium borosilicate or calcium aluminum borosilicate and aluminum.

Among the organic dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green 5 (CI 61 570), D&C Yellow 10 (CI 77 002), D&C Green 3 (CI 42 053), D&C Blue 1 (CI 42 090).

An example of a lake that may be mentioned is the product known under the name D&C Red 7 (CI 15 850:1).

Liposoluble Dyes

For the purposes of the invention, the term "liposoluble dye" means any natural or synthetic, generally organic compound, which is soluble in an oily phase or in solvents that are miscible with the oily phase, and which is capable of imparting color.

As liposoluble dyes that are suitable for use in the invention, mention may notably be made, for instance, of the liposoluble dyes DC Red 17, DC Red 21, DC Red 27, DC Green 6, DC Yellow 11, DC Violet 2, DC Orange 5, Sudan red and Sudan brown.

As illustrations of natural liposoluble dyes, mention may be made particularly of carotenes, for instance ß-carotene, a-carotene and lycopene; quinoline yellow; xanthophylls such as astaxanthin, antheraxanthin, citranaxanthin, cryptoxanthin, canthaxanthin, diatomoxanthin, flavoxanthin, fucoxanthin, lutein, rhodoxanthin, rubixanthin, siphonaxanthin, violaxanthin, zeaxanthin; annatto; curcumin; quinizarin (Ceres Green BB, D&C Green No. 6, CI 61565, 1,4-di-p-toluidinoanthraquinone, Green No. 202, quinazine green SS) and chlorophylls.

According to a preferred embodiment of the invention, the composition comprises from 0.01% to 20% by weight, notably from 1% to 15% by weight and even more particularly from 2% to 13% by weight of dyestuff(s), relative to the weight of the composition. The composition may also be free of dyestuff(s).

Optional Adjuvants

In the context of the present invention, the composition may also contain at least one optional adjuvant chosen from those usually used in the cosmetics field, in particular for makeup and/or care compositions for the skin and the lips.

Examples that may be mentioned include lipophilic thickeners, such as silicas, organic gelling agents (organogelators), clays, fillers, preserving agents, antioxidants, complexing agents, solvents, fragrances, and the like.

These adjuvants and the concentrations thereof must be such that they do not modify the property desired for the composition of the invention.

The composition according to the invention may optionally comprise water in a content not exceeding 5% by weight, preferably not exceeding 2% by weight, relative to the total weight of the composition. Even more advantageously, the water content, if the composition comprises any, does not exceed 1% by weight, notably does not exceed 0.5% by weight and even more particularly does not exceed 0.2% by weight, relative to the total weight of the composition.

The examples that follow are presented as nonlimiting illustrations of the invention.

Unless otherwise indicated, the amounts shown are expressed as mass percentages of starting materials.

The starting materials are referred to by their chemical or INCI name.

EXAMPLES

Example 1

The following compositions, the list of ingredients and the contents of which are collated in the table below, are prepared:

TABLES 1

| Ingredients | Composition 1 invention | Comparative composition 2 |
|---|---|---|
| *Limnanthes alba* (Meadowfoam) Seed Oil (Fancor meadowfoam seed oil, sold by the company Elementis) | 15 | — |
| *Olea europaea* (Olive) Fruit Oil (Refined Organic Olive Oil, sold by AarhusKarlshamn) | 15 | — |
| Caprylic/Capric Triglyceride (Masester E7000 Medium Chain Triglycerides, sold by the company Musim Mas) | 26 | 26 |
| *Ricinus communis* Seed Oil (Pharmaceutical Castor Oil E.P., sold by the company Olvea) | — | 30 |
| *Helianthus annuus* (Sunflower) Seed Wax (Sunflower Wax Double Refined, sold by the company Koster Keunen) | 4 | 4 |
| *Euphorbia cerifera* (Candelilla) Wax (820 Light Special Candelilla Real, sold by the company Multiceras) | 4 | 4 |
| *Oryza sativa* (Rice) Bran Wax (NC 1720, sold by the company Cera Rica Noda) | 6 | 6 |
| Bis-Diglyceryl Polyacyladipate-2 (Softisan 649, sold by the company Cremer Oleo) | 20 | 20 |
| Red 7 | 3.7 | 3.7 |
| Red 28 Lake | 3.4 | 3.4 |
| Iron oxide | 2.5 | 2.5 |
| Titanium dioxide | 0.4 | 0.4 |

Preparation Process

1. The pigments are ground in the portion of oil(s) required for good dispersion, using a three-roll mill or a ball mill.
2. The waxes and the remainder of the oils are heated to 98° C. in a suitable container, so as to obtain a homogeneous mixture.
3. The pigments are added to the mixture from the preceding step, with stirring.
4. The pasty substance is then added at 98° C., with stirring.
5. Once the mixture is thoroughly homogenized, the preparation is maintained at room temperature for casting 24 hours later.
6. After 24 hours, the formulation is reheated to 98° C. and the composition is cast in molds preheated to 42° C.
7. After waiting for the surface to set, the surface is leveled off.
8. The molds are placed at −25° C. until the mold returns to a temperature of 4° C.
9. The wands are removed from the molds.

Evaluation of the Compositions

TABLES 2

| | Composition 1 invention | Comparative composition 2 |
|---|---|---|
| Hardness | 142 $Nm^{-1}$ | 176 $Nm^{-1}$ |
| Appearance of the wand body (after manufacture) | Homogeneous, satiny | Homogeneous, satiny |
| Application | Good glidance, comfortable, creamy deposit with good coverage. Non-tacky deposit which does not migrate and has good staying power. | Harder wand, with acceptable glidance, but which deposits less. Finer, less comfortable (less occlusive, less creamy) deposit with lower coverage. The deposit is not tacky, does not migrate and has good staying power. |
| Stability | The wand body is homogeneous, its shape has not changed, nor has its odor or its color. Absence of exudation at all the temperatures 4° C., 20° C. and 45° C. at 1 week, 1 month and 2 months, in the upright position and in the inverted position. | Nothing to report except for the appearance droplet(s) of exudation of oil on the beveled edge of the wand body, from 1 week of storage at 45° C. in the inverted position. This phenomenon is still observed after 1 and 2 months of storage in this position. |

The invention claimed is:

1. A solid composition for making up and/or caring for skin and/or lips, in wand form, comprising:
   - sunflower wax;
   - candelilla wax;
   - at least one triglyceride selected from the group consisting of triglycerides of caprylic acid, of capric acid, of caprylic/capric acid, and mixtures thereof;
   - at least one plant oil which is not castor oil; and
   - at least one polyester derived from the condensation of a linear or branched $C_6$-$C_{10}$ dicarboxylic acid and of an ester of diglycerol and of optionally hydroxylated, linear or branched $C_6$-$C_{20}$ monocarboxylic acids,
   - wherein castor oil, if present in the composition, is present in a content not exceeding 5% by weight relative to the total weight of the composition and
   - wherein silicone oil(s) and apolar hydrocarbon-based oil(s) resulting from the conversion of petroleum, if present in the composition, is/are present in a content less than or equal to 7% by weight relative to the total weight of the composition.

2. The composition of claim 1, wherein a content of sunflower wax present in the composition is from 1% to 9% by weight relative to the total weight of the composition.

3. The composition of claim 1, wherein a content of candelilla wax present in the composition is from 0.25% to 7% by weight relative to the total weight of the composition.

4. The composition of claim 1, wherein a content of triglyceride(s) present in the composition is at least 10% by weight relative to the total weight of the composition.

5. The composition of claim 1, wherein the plant oil(s) which is/are not castor oil is/are selected from the group consisting of olive oil, coco oil, coconut oil, coconut kernel oil, jojoba oil, ximenia oil, annatto oil, pracaxi oil, coriander seed oil, macadamia oil, passionflower oil, argan oil, sesame oil, sunflower oil, grape seed oil, avocado oil, *Rosa canina* oil, apricot kernel oil, linseed oil, sweet almond oil, cottonseed oil, soybean oil, rapeseed oil, groundnut oil, kaya oil, marula oil, camelina oil, wheat germ oil, maize oil, maize germ oil, rice bran oil, alfalfa oil, poppy oil, pumpkin oil, marrow oil, hazelnut oil, blackcurrant oil, evening primrose oil, millet oil, barley oil, quinoa oil, rye oil, safflower oil, candlenut oil, limnanthes oil, black cumin oil, buriti oil, sandalwood nut oil, babassu oil, a liquid fraction of shea butter, and a liquid fraction of cocoa butter, and mixtures thereof.

6. The composition of claim 1, wherein a content of plant oil which is not castor oil present in the composition is at least 5% by weight relative to the total weight of the composition.

7. The composition of claim 1, wherein the content of castor oil, if present in the composition, is less than 2% by weight relative to the total weight of the composition.

8. The composition of claim 1, wherein the composition further it comprises at least one polar hydrocarbon-based wax, other than sunflower wax and candelilla wax.

9. The composition of claim 8, wherein a content of polar hydrocarbon-based wax(es), other than sunflower wax and candelilla wax, is from 0.25% to 9% by weight relative to the total weight of the composition.

10. The composition of claim 1, wherein the composition further comprises at least one apolar hydrocarbon-based wax in a content not exceeding 2% by weight relative to the total weight of the composition.

11. The composition of claim 1, wherein a combined content of sunflower wax, candelilla wax, and polar hydrocarbon-based wax(es) is from 6% to 26% by weight relative to the total weight of the composition.

12. The composition of claim 1, wherein a content of the at least one polyester is from 5% to 35% by weight relative to the total weight of the composition.

13. The composition of claim 1, wherein the composition further comprises at least one hydrocarbon-based pasty compound other than the at least one polyester selected from the group consisting of plant butters, partially or totally hydrogenated plant oils, saturated or unsaturated, linear or branched, optionally monohydroxylated or polyhydroxylated $C_{12}$-$C_{18}$ fatty acid triglycerides, esters of diol dimer or of alcohol or of polyol and of diacid dimer, and mixtures thereof.

14. The composition of claim 1, wherein silicone oil(s) and apolar hydrocarbon-based oil(s) resulting from the conversion of petroleum, if present in the composition, is/are present in a content less than or equal to 5% by weight relative to the total weight of the composition.

15. The composition of claim 1, wherein the composition further comprises at least one $C_{10}$-$C_{26}$ alcohol in a content of from 1% to 20% by weight relative to the total weight of the composition.

16. The composition of claim 1, wherein the composition further comprises at least one dyestuff selected from the group consisting of that the dyestuff is chosen from pigments, fat-soluble dyes, and mixtures thereof.

17. The composition of claim 1, wherein the composition further comprises water in a content not exceeding 2% by weight relative to the total weight of the composition.

18. The composition of claim 1, wherein the composition is in the form of a wand, having a hardness of between 70 and 200 $Nm^{-1}$ at 20° C. and at atmospheric pressure.

19. A process for making up and/or caring for skin and/or lips, comprising applying the composition of claim 1 to skin and/or lips.

20. The composition of claim 1, wherein the composition further comprises at least one polar hydrocarbon-based wax, other than sunflower wax and candelilla wax, selected from the group consisting of:

i) waxes of formula RICOOR2 in which R1 and R2 represent linear, branched or cyclic aliphatic chains in which the number of atoms is from 10 to 50, which may contain a heteroatom, and having a melting point of from 40 to 120° C.;

ii) dicarboxylic acid diester waxes of general formula R3—(—OCO—R4—COO—R5), in which R3 and R5 are identical or different and represent a C4-C30 alkyl group, and R4 represents a linear or branched C4-C30 aliphatic group which may or may not contain one or more unsaturations;

iii) partial or total esters of a saturated C16-C30 carboxylic acid with glycerol;

iv) waxes of animal or plant origin, other than sunflower wax and candelilla wax;

v) waxes obtained by hydrogenation of animal or plant oils; and vi) mixtures thereof.

21. The composition of claim 14, wherein the composition further comprises at least one $C_{10}$-$C_{26}$ alcohol in a content of from 1% to 7% by weight relative to the total weight of the composition.

* * * * *